United States Patent [19]

Russo

[11] Patent Number: 5,267,968
[45] Date of Patent: Dec. 7, 1993

[54] RETENTION BOLSTER FOR PERCUTANEOUS CATHETERS

[76] Inventor: Ronald D. Russo, 8 Candleberry Rd., Barrington, R.I. 02806

[21] Appl. No.: 911,171

[22] Filed: Jul. 9, 1992

[51] Int. Cl.⁵ .............................................. A61M 5/32
[52] U.S. Cl. ...................................................... 604/174
[58] Field of Search ............... 604/174, 177, 178, 250; 215/355

[56] References Cited

U.S. PATENT DOCUMENTS

| 1,696,763 | 12/1928 | Hare | 604/179 |
| 3,444,861 | 5/1969 | Schulte | 604/175 X |
| 3,721,229 | 3/1973 | Panzer | 604/174 X |
| 4,645,504 | 2/1987 | Byers | 604/174 X |
| 4,668,225 | 5/1987 | Russo et al. | 604/270 |

FOREIGN PATENT DOCUMENTS

2057269 4/1981 United Kingdom ................. 604/174

OTHER PUBLICATIONS

Wilson-Cook Catalog, p. 67, product description sheet for Russell Gastrostomy Trays.
Superior Biosystems Inc., product description sheet for Caluso Gastrostomy Tube and Jejunal Feeding Tube.
Superior Biosystems Inc., product description sheet for PEDI PEG Silicone Gastrostomy Feeding Tube Kit.
Superior Biosystems Inc., product description sheet for Flow-Thru Replacement Gastrostomy Tube.
Bard Interventional Products, product description sheet for AEI Silicone Replacement Gastrostomy.

*Primary Examiner*—Robert P. Swiatek

[57] ABSTRACT

A retention bolster for a percutaneous catheter is disclosed having a convexly curved exterior surface which contacts the epidermal surface of a patient. The retention bolster slides over a catheter until contacting the skin of the patient at the catheter exit site. When secured in place, the retention bolster rocks along contacting portions between its convexly curved surface and the epidermal surface of the patient in response to movement of the catheter about the exit site, thereby alleviating the added pressure that would otherwise be applied by this movement. Upon the release of lateral pressure against the catheter device, the bolster returns to its original upright position. In a second disclosed embodiment, a flange is provided which extends from the main body of the bolster which defines a bore that is also sized for slidably receiving and supporting the catheter, and which provides for angled attachment of the catheter relative to its exit site.

14 Claims, 2 Drawing Sheets

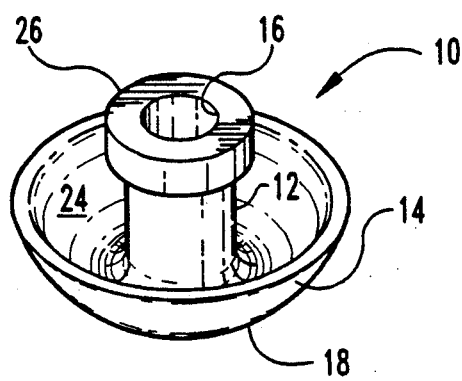
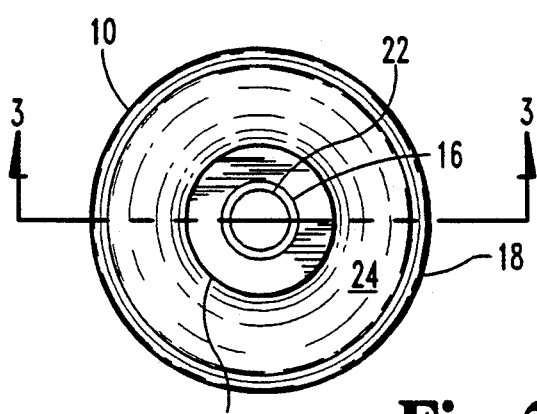
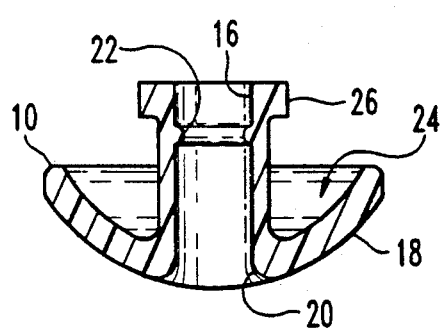
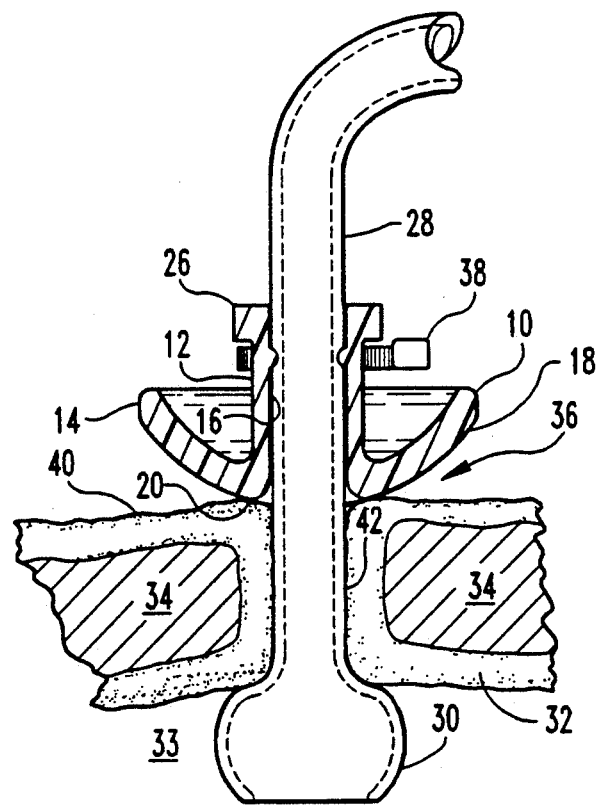

RETENTION BOLSTER FOR PERCUTANEOUS CATHETERS

BACKGROUND OF THE INVENTION

This invention relates generally to medical devices and, more particularly, to a retention bolster for adjustably supporting a tubular medical device adjacent an epidermal surface.

Typically, a retention bolster is positioned at the exit site of a catheter to hold the catheter securely against the patient's body. The bolster is locked in place to maintain support of the catheter and prevent bending or crimping of the catheter at the exit site. So positioned, bolsters apply continual, direct pressure to the skin at the exit site of the catheter from the patient's body, sometimes having the effect of inhibiting the healing of the skin at the exit site of the catheter and possibly causing necrosis due to the applied pressure.

Bolsters for supporting tubular medical devices, such as catheters, outside the body have generally focused on maintaining the secure anchoring of the device to the patient. To provide lateral support, bolsters have employed flanges, cross-bars, or discs for contacting the epidermal surface. Prior attempts at minimizing the continual, direct pressure applied by these supports have included the placement of pads or webs underneath the cross-bars, for example, of the bolster. Pads and webs, however, have actually tended to increase the localized pressure at the exit site, especially when the catheter, either accidentially or intentionally, is moved thereabout. Further, as percutaneous catheter placement techniques have become increasingly common, catheters have been increasingly used for longer periods of time. As such, infections of the skin at the catheter exit site have become increasingly common as well.

One particular application magnifying the deficiencies of existing bolsters involves the use of percutaneous gastrostomy catheters (PEG tubes) to provide long term access into the stomach. A PEG tube is maintained at its stoma exit site by a retention bolster for several months while it is used to provide access into the stomach. Existing bolsters, however, which remain inflexibly clamped to maintain the catheter in position during use, do not accommodate the unavoidable movements of the catheter during this long period of time. As the catheter is moved about, either accidentally or as it is handled by attending medical personnel, additional pressure is often applied causing the bolster to dig into the skin surface and resulting in pressure sores and maceration of the stoma site. As a result of these deficiencies, existing bolsters have often been the source of irritation and infections of the skin.

A need, therefore, exists for an improved retention bolster for use adjacent an epidermal surface to support a tubular medical device. Such a bolster should securely hold a catheter in place while exerting minimal amounts of pressure at the catheter exit site, and preferably would permit movement of the catheter about the stoma exit site without causing or aggravating injury thereat.

SUMMARY OF THE INVENTION

The present invention provides a new retention bolster which securely and safely supports a percutaneous catheter, or similar device, against an epidermal surface, and allows for movement of the catheter about its exit site without causing or aggravating injury to the patient. The retention bolster includes means for securely attaching to the catheter, and a convexly curved surface for contacting the epidermal surface of the patient. The bolster attaches to the catheter with the convexly curved surface contacting the epidermal surface of the patient, and rocks along contacting portions between the convexly curved surface and the epidermal surface in response to movement of the tubular medical device about its exit site. In this way, a rocking movement about the stoma exit site is permitted without causing or aggravating injury thereat. Upon the release of lateral pressure against the catheter device, the bolster returns to its original upright position. In a second disclosed embodiment, a flexible flange is provided which includes means for receiving and securely attaching the catheter at a right angle relative to the exit site.

One object of the present invention is to provide an improved retention bolster for use adjacent an epidermal surface to support a tubular medical device.

Another object of the present invention is to provide a retention bolster which securely holds a catheter in place while exerting minimal amounts of pressure at the catheter exit site.

Still another object of the present invention is to provide an adjustable retention bolster which minimizes the amount of applied pressure at the stoma site, and accommodatingly adjusts the application of pressure as the retained catheter is moved thereabout.

It is a further object of the present invention to provide a retention bolster which applies minimal contact to the skin, thereby allowing for aeration of the stoma site to promote healing.

A further object of the present invention is to provide a rockably adjustable retention bolster which permits both rotation of the catheter and rocking of the catheter in any direction.

Still yet another object of the present invention is to provide a rockably adjustable retention bolster which is self-centering so as to return the catheter to its original position after being flexed therefrom.

Another object of the present invention is to provide a retention bolster which holds a catheter at a right angle relative to the epidermal surface.

Still another object of the present invention is to provide a retention bolster which is inexpensive to manufacture and adapted to fit various sizes of catheters and other tubular medical devices.

These and other related objects and advantages of the present invention will become apparent from the following drawings and written description.

BRIEF DESCRIPTION OF THE DRAWINGS

FIG. 1 is a perspective view of a rockably adjustable retention bolster according to one embodiment of the present invention.

FIG. 2 is a top plan view of the rockably adjustable retention bolster of FIG. 1.

FIG. 3 is a side cross-sectional view taken along lines 3—3 of the rockably adjustable retention bolster of FIG. 2.

FIG. 4 is a partial side cross-sectional view of the rockably adjustable retention bolster of FIG. 1 releasably attached to a percutaneous gastrostomy catheter and cooperating therewith to maintain pressure at a stoma exit site.

DESCRIPTION OF THE PREFERRED EMBODIMENT

Figure 5:
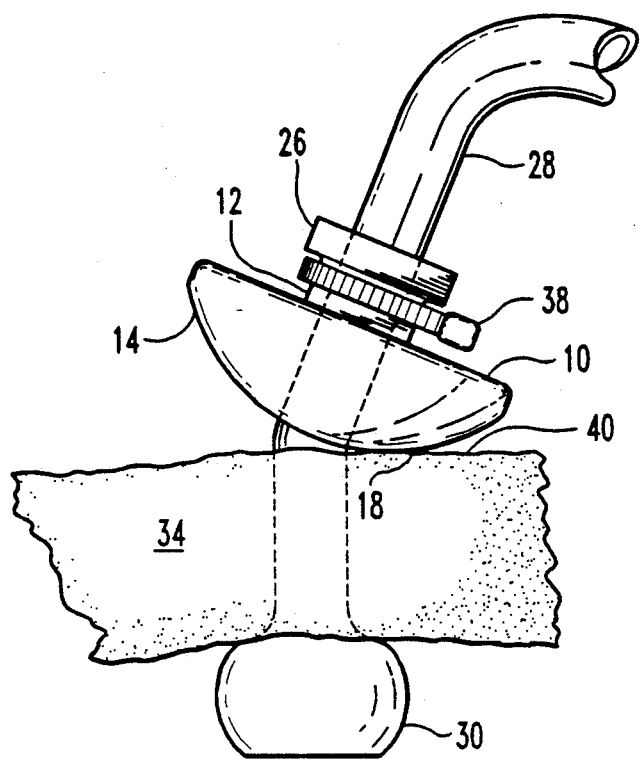
FIG. 5 is a side elevational view of the rockably adjustable retention bolster of FIG. 4 depicted in an adjusted position in response to movement of the percutaneous gastrostomy catheter.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring now to FIGS. 1-3, a retention bolster 10 is shown including an upstanding cylindrical portion 12 and a convexly curved exterior portion 14. Cylindrical portion 12 defines a longitudinal bore 16 extending therethrough and through curved exterior portion 14, wherein bore 16 is sized for slidably receiving and supporting a tubular medical device, such as a catheter, therein. Curved exterior portion 14 includes annular convex surface 18 which has a convexly uniform curvature centered about, and curving away from bore 16 for contacting an epidermal surface. Conversely, the opposing side to annular convex surface 18 forms a cooperating concave surface 24, wherein the general configuration of a bowl is assumed. Extending between longitudinal bore 16 and annular convex surface 18 is curvilinear surface 20 which provides a smooth transition therebetween. As such, annular convex surface 18 and curvilinear surface 20 of convexly curved exterior portion 14 provide a smooth curved surface which securely holds a catheter to the skin without digging into or otherwise irritating or damaging the epidermal surface.

In the preferred embodiment, retention bolster 10 is of a one-piece molded plastic construction. Preferably, retention bolster 10 is constructed of clear medical grade silicon or synthetic rubber, such as Monsanto SANTOPRENE® or Shell Chemical KRATON®. In either material, a hardness of 50 Durometer on a Shore A scale is desired for providing both strength and resiliency. As such, retention bolster 10 is resiliently deformable to provide a mechanism by which retention bolster 10 releasably attaches to a catheter. For example, bore 16 may be sized smaller in diameter than the catheter for receipt therein so that retention bolster 10 resiliently flexes to receive the catheter through the bore, thereby clamping the catheter in the bore. In the preferred embodiment, bore 16 of cylindrical portion 12 includes a reduced diameter portion 22. Cylindrical portion 12 resiliently flexes in the vicinity of reduced diameter portion 22 to receive the catheter, thereby causing the reduced diameter portion to clamp the catheter in bore 16.

For enhanced clamping and sealing of the catheter in bore 16, retention bolster 10 also is adapted for receiving a clamping element about cylindrical portion 12. Retention bolster 10 includes a peripheral undercut 24 in curved exterior portion 14 to allow clearance for receiving an adjustable clamping element. Cylindrical portion 12 also includes an annular flange 26, which acts to retain a clamping element in place, once received.

Referring now to FIG. 4, retention bolster 10 is shown cooperating with a percutaneous gastrostomy catheter 28 having an expanded distal tip 30 for contacting stomach wall or lining 32 of stomach 33. Catheter 28 is maintained clamped across epidermal layer 34 by the compressive action between retention bolster 10 and expanded distal tip 30. As such, expanded distal tip 30 exerts a uniform pressure on stomach wall 32 to maintain a seal therebetween and ensure rapid healing. Similarly, retention bolster 10 exerts an equal and opposite pressure at stoma exit site 36 necessary to maintain the compressive action.

As shown in FIG. 4, retention bolster 10 includes an adjustable clamp 38 about cylindrical portion 12. Clamp 38 adjusts to tighten about cylindrical portion 12 to both clamp and seal catheter 28 within bore 16. As such, retention bolster 10 is held in place contacting the epidermal surface 40. In the orientation shown in FIG. 4, catheter 28 is in its centered position with curvilinear surface 20 of curved exterior portion 14 minimally contacting the epidermal surface. As such, stoma exit site 36 is aerated for rapid healing of stoma tract 42. Further, because of the minimal contact area and pressure, catheter 28 is able to be rotated 360 degrees within stoma tract 42 without damaging the epidermal surface.

Referring also to FIG. 5, catheter 28 is shown rocked about the stoma exit site along convex surface 18 and epidermal surface 40 in response to movement of the catheter. As an external force is applied to the catheter, such as by positioning the catheter to introduce nutritional liquids into the stomach via the catheter, retention bolster 10 rocks to reduce the pressure on epidermal surface 40 and to move its point of application on the epidermal surface. Because the center of the compressive action between the retention bolster and the expanded tip is shifted away from the exit site, an overturning moment is created which acts to center the catheter once the external force is removed. As such, retention bolster 10 is self-centering. Further, by being self-centering in returning catheter 28 to the orientation shown in FIG. 4, retention bolster 10 acts to minimize inward migration of the expanded distal tip 30 into the stomach wall 32.

Figure 6:
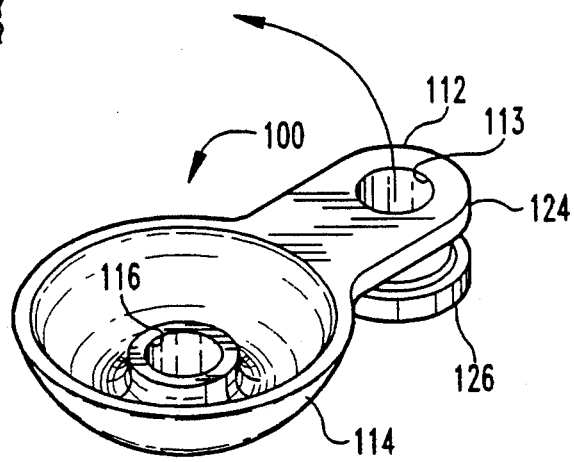
FIG. 6 is a perspective view of a rockably adjustable retention bolster according to another embodiment of the present invention shown in its free, unrestrained position.
Figure 7:
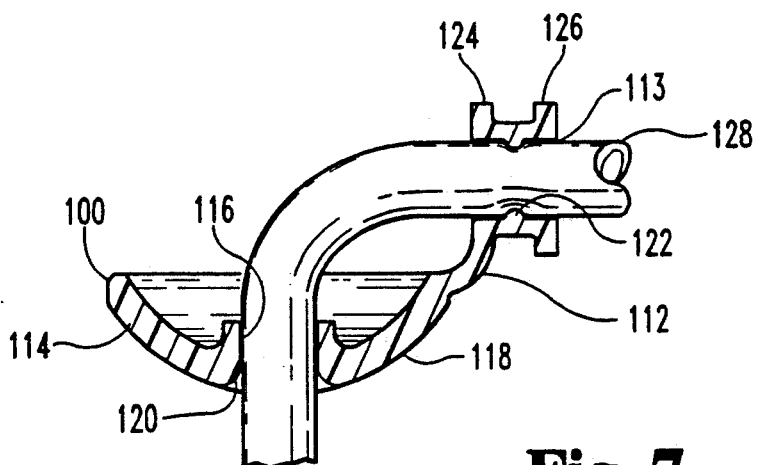
FIG. 7 is a partial side cross-sectional view of the rockably adjustable retention bolster of FIG. 6 shown in its restrained position bending a catheter between the bolster's main body and a flange extending therefrom.

In many applications it is desirous to maintain the catheter at an angle relative the exit site of the patient to prevent the catheter from damage as the patient moves about, such as by rolling over or sitting up. Referring now to FIGS. 6 and 7, an alternate embodiment of a retention bolster 100 is shown including convexly curved exterior portion 114. Curved exterior portion 114 defines a first bore 116 extending therethrough and through curved exterior portion 114, wherein bore 116 is sized for slidably receiving and supporting a tubular medical device, such as a catheter, therein. Curved exterior portion 114 includes an annular convex surface 118 which has a convexly uniform curvature centered about, and curving away from bore 116 for contacting an epidermal surface and a smooth curvilinear surface 120 extending between surface 118 and bore 116. Unlike retention bolster 10, retention bolster 100 also includes an outwardly extending flange 112 which defines an additional bore 113 that is also sized for slidably receiving and supporting a tubular medical device, and which provides for angled attachment of a catheter relative to its exit site.

Bore 113 within flange 112 includes a reduced diameter portion 122. Flange 112 resiliently flexes to receive a catheter, thereby causing reduced diameter portion 122 to clamp a catheter within bore 113. For enhanced clamping of the catheter within bore 113, flange 112 also is adapted for receiving a clamping element. Flange 112 includes annular flanges 124 and 126 which maintain a clamping element in place once received. As shown in FIG. 6, retention bolster 100 is in its free unrestrained position with bore 113 aligned substantially parallel with bore 116. Because retention bolster 100 is resiliently deformable, it can assume a restrained position as shown in FIG. 7. Referring now also to FIG. 7, retention bolster 100 is shown with a catheter 128 received through bores 113 and 116, wherein the catheter is bent at a right angle by the force exerted when flange 112 is resiliently flexed from its free, unrestrained position. As such, retention bolster 100 maintains the existing portion of catheter 128 substantially parallel with the epidermal surface. Depending upon the position at which flange 112 is secured to catheter 128 and the interacting forces therebetween, catheter 128 may also be bent to extend within a range of desired angles.

In the preferred embodiment, retention bolster 100 also is of a one-piece molded plastic construction. As previously discussed, retention bolster 10 is preferably constructed of clear medical grade silicon or synthetic rubber, such as Monsanto SANTOPRENE ® or Shell Chemical KRATON ®. In either material, a hardness of 50 Durometer on a Shore A scale is desired for providing both strength and resiliency. As such, retention bolster 100 is resiliently deformable to provide a mechanism by which retention bolster 100 releasably attaches to a catheter.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A retention bolster for retaining a tubular medical device against the epidermal surface at the exit site of the device from the body of a patient, said bolster comprising:
    a main body having a convexly curved exterior surface portion for contacting the epidermal surface and an upstanding cylindrical portion extending therefrom; and
    means for securely attaching said main body to the tubular medical device including a longitudinal bore adapted for slidably receiving the tubular medical device therethroug, said longitudinal bore extending through said curved exterior portion and said upstanding cylindrical portion of said main body; and means for clamping the tubular medical device within said longitudinal bore; and
    wherein said main body is attachable to the tubular medical device with said convexly curved exterior portion in contact with the epidermal surface, and wherein said main body is rockable along contacting portions between said convexly curved exterior portion and the epidermal surface in response to movement of the tubular medical device about the exit site.

2. The retention bolster of claim 1, wherein:
    said convexly curved exterior portion of said main body includes an annular convex surface having a convexly uniform curvature centered about, and curving away from said longitudinal bore; and
    said main body rocks along contacting portions between said annular convex surface and the epidermal surface.

3. The retention bolster of claim 2, wherein a curvilinear surface extends between said longitudinal bore and said annular convex surface.

4. The retention bolster of claim 3, and further comprising:
    a resiliently flexible flange attached to said main body; and
    a second bore disposed in said flange; and
    wherein said flange resiliently flexes to a position aligning said second bore at an angle relative said longitudinal bore when the tubular medical device is received in said longitudinal and second bores, said resiliently flexible flange bending the tubular medical device between said longitudinal bore of said main body and said second bore of said flange.

5. The retention bolster of claim 1, wherein:
    said upstanding cylindrical portion is resiliently flexible; and
    said longitudinal bore includes a reduced diameter portion;
    said upstanding cylindrical portion resiliently flexing to receive the tubular medical device through said reduced diameter portion, thereby causing said reduced diameter portion to clamp the tubular medical device in said longitudinal bore.

6. The retention bolster of claim 5, and further comprising:
    a clamp disposed about said upstanding cylindrical portion;
    said clamp being adjustable to clamp across said reduced diameter portion, thereby causing said reduced diameter portion to clamp the tubular medical device in said longitudinal bore.

7. The retention bolster of claim 6, wherein:
    the tubular medical device is a percutaneous gastrostomy catheter; and
    wherein said retention bolster cooperates with the percutaneous gastrostomy catheter to maintain said convexly curved exterior portion of said main body against the epidermal surface.

8. A retention bolster for retaining a catheter against the epidermal surface at the exit site of the catheter from the body of a patient, said bolster comprising:
    a main body having a convexly curved exterior portion for contacting the epidermal surface;
    a first bore adapted for slidably receiving the catheter therethrough, said first bore extending through said main body and said convexly curved exterior portion;
    a flange attached to said main body; and
    a second bore extending through said flange and adapted for slidably receiving the catheter therethrough; and
    wherein the catheter is slidably receivable through said first and second bores, the catheter bending between said first and second bores, and wherein said main body is attachable to the catheter with said convexly curved exterior portion in contact with the epidermal surface, and wherein said main body is rockable along contacting portions between said curved exterior portion and the epidermal surface in response to movement of the catheter about the exit site.

9. The retention bolster of claim 8, wherein:

said flange is resiliently flexible between a first unrestrained position with said second bore aligned substantially parallel with said first bore and a second restrained position with said second bore aligned substantially perpendicular relative said first bore; and said flange resiliently flexes to its second restrained position when the catheter is received through said first and second bores thereby maintaining an approximate right angle bend in the catheter between said first and second bores.

10. The retention bolster of claim 9, wherein:

said curved exterior portion of said main body includes an annular convex surface having a convexly uniform curvature centered about, and curving away from said first bore; and said main body rocks along contacting portions between said annular convex surface and the epidermal surface.

11. The retention bolster of claim 10, wherein a curvilinear surface extends between said first bore and said annular convex surface.

12. The retention bolster of claim 8, wherein:

said second bore includes a reduced diameter portion; and said flange resiliently flexes to receive the catheter through said reduced diameter portion, thereby causing said reduced diameter portion to clamp the catheter in said second bore.

13. The retention bolster of claim 12, and further comprising:

a clamp disposed about said second bore; and wherein said clamp is adjustable to clamp across said reduced diameter portion, thereby causing said reduced diameter portion to clamp the catheter in said second bore.

14. The retention bolster of claim 13, wherein:

the catheter is a percutaneous gastrostomy catheter;

wherein the retention bolster cooperates with the percutaneous gastrostomy catheter to maintain said convexly curved exterior portion of said main body adjacent the epidermal surface.

* * * * *

UNITED STATES PATENT AND TRADEMARK OFFICE
CERTIFICATE OF CORRECTION

PATENT NO. : 5,267,968
DATED : December 7, 1993
INVENTOR(S) : Ronald D. Russo

It is certified that error appears in the above-identified patent and that said Letters Patent is hereby corrected as shown below:

In column 1, line 31, please change "accidentially" to --accidentally--.
In column 5, line 60, please change "therethroug" to --therethrough--.

Signed and Sealed this

Twenty-ninth Day of November, 1994

Attest:

BRUCE LEHMAN

Attesting Officer     Commissioner of Patents and Trademarks